United States Patent
Teoh et al.

(10) Patent No.: US 7,179,415 B2
(45) Date of Patent: Feb. 20, 2007

(54) METHOD OF MAKING A NON-TACKY, POWDER-FREE NEOPRENE ARTICLE LIKE A GLOVE OR CONDOM

(75) Inventors: Seng Chin Teoh, Hertfordshire (GB); Seong Fong Chen, Penang (MY)

(73) Assignee: Regent Medical Limited, Manchester (GB)

( * ) Notice: Subject to any disclaimer, the term of this patent is extended or adjusted under 35 U.S.C. 154(b) by 443 days.

(21) Appl. No.: 10/399,451

(22) PCT Filed: Oct. 22, 2001

(86) PCT No.: PCT/GB01/04676

§ 371 (c)(1), (2), (4) Date: Jul. 7, 2003

(87) PCT Pub. No.: WO02/32475

PCT Pub. Date: Apr. 25, 2002

(65) Prior Publication Data

US 2004/0096686 A1 May 20, 2004

(30) Foreign Application Priority Data

Oct. 20, 2000 (GB) ................................. 0025777.4

(51) Int. Cl.
*B29C 41/14* (2006.01)
*A61F 6/04* (2006.01)
*A41D 19/015* (2006.01)

(52) U.S. Cl. ...................... 264/494; 264/255; 264/301; 264/307; 2/168; 2/16; 2/161.7; 128/844

(58) Field of Classification Search .................... None
See application file for complete search history.

(56) References Cited

U.S. PATENT DOCUMENTS

| 2,060,343 A | 11/1936 | Palicki |
| 2,458,221 A | 1/1949 | Svendsen et al. |
| 5,881,387 A * | 3/1999 | Merovitz et al. ............ 2/161.7 |
| 6,195,805 B1 * | 3/2001 | Bourne et al. ................ 2/168 |
| 6,306,514 B1 * | 10/2001 | Weikel et al. .............. 428/451 |

FOREIGN PATENT DOCUMENTS

| GB | 445534 | 9/1934 |
| WO | 9943739 | 9/1999 |
| WO | 0015353 | 3/2000 |

* cited by examiner

*Primary Examiner*—Edmund H. Lee
(74) *Attorney, Agent, or Firm*—Stevens, Davis, Miller & Mosher, L.L.P.

(57) ABSTRACT

A method of making a non-tacky, powder-free neoprene article, preferably by dipping a former in a neoprene or neoprene copolymer latex, comprises the use of one or more anionic anti-tack agents in order to prevent any significant development of tack for a period of up to at least seven days when the article is stored at 70° C. or at least 90 days when stored at 45° C. Preferably, the article is a glove or condom further comprising a layer of hydrogel.

19 Claims, No Drawings

METHOD OF MAKING A NON-TACKY, POWDER-FREE NEOPRENE ARTICLE LIKE A GLOVE OR CONDOM

This invention relates to synthetic rubber articles, particularly gloves, and to a process for their preparation, and more particularly to synthetic rubber articles made from neoprene (polychloroprene) or a neoprene copolymer.

During the last few years, allergenic problems associated with gloves made from natural rubber have led to the development of a variety of gloves made from synthetic elastomeric materials which are substantially non-allergenic. These include gloves made from neoprene or neoprene copolymers, described for example in WO 96/40306 (Baxter International, Inc.) Certain neoprene copolymers (such as, for example, Neoprene 750, available from Dupont) are particularly preferred, as they enable the formulation of gloves having a softness and flexibility very similar to that of natural rubber. Synthetic rubber gloves can, however, be difficult to don and conventionally this problem has been addressed by coating the interior of the glove with lubricant powders of one sort or another. However, powdered gloves, particularly powdered examination and surgical gloves, are disadvantageous in that there is a potential risk of contamination and inflammation to the patient if powder is introduced into a wound or an incision. Another problem with gloves made from synthetic elastomers such as neoprene is that the gloves can be 'tacky' or 'sticky' and this can lead to problems with the finished glove sticking either to itself or to other gloves and/or to packaging material. Strictly, 'tackiness' relates to the adherence of an article to itself or an identical article, whereas 'stickiness' is used to described the adherence of an article to other material.

A powder-free synthetic medical glove made from neoprene copolymer is described in WO 99/43739 (Allegiance Healthcare Corporation) and the glove is said to possess minimal stickiness. To obtain the non-sticky powder-free glove, a lengthy multi-step process is employed, which includes the steps of dipping a former (coated with latex) into a powdered slurry of surfactant, powder, silicone and water (to reduce stickiness), curing, stripping, everting the glove and then chlorinating in order to reduce tackiness and to remove the powder. Furthermore, a second manual eversion step is then required in order to return the user-contacting surface to the inside of the glove. The process of WO 99/43739 is complicated and time-consuming, and has the serious disadvantage of requiring chlorination which is both expensive and can potentially have deleterious effects on the properties of the finished glove. The high level of chlorination needed to properly remove tackiness and the powder from the glove in WO 99/43739 is likely to lead to discoloration of the rubber and may also adversely affect its physical properties.

In addition, whilst providing an initial reduction in the level of tack, chlorination (and halogenation generally) may not prevent the development of tack over the medium to long term. Chlorination is, therefore, only a partial solution to the problem of tack development.

There have been other approaches to the problem of tackiness in articles made from rubber, although none of them is entirely satisfactory. As mentioned above, various sorts of powders have been used, including corn starch, absorbable dusting powder (modified cross-linked corn starch) and talc. Whilst powders do provide acceptable tack reduction for a number of applications, they are unsuitable for certain articles, in particular medical examination and surgical gloves, owing to the risk of contamination. Silicone oils have been used to reduce tackiness, although as with halogenation, these oils only provide a partial reduction in tackiness. They do not prevent the development of tackiness over the long term. Various polymer coatings such as hydrogels, urethanes and polyethylenes have also been used to detackify rubber by providing a 'slippery' coating. Generally, however, these slip-coatings are only suitable for use on the internal surface of an article (for example, the inside of a glove). The use of these coatings on the outside or external surface of the article usually results in the article being too slippery for its intended use and this presents problems with handleability. Cross-linking of rubber (i.e. vulcanisation) gives some short term reduction in the degree of tackiness, although it does not prevent the development of tack over the longer term.

We have now devised a way of providing non-tacky, powder-free neoprene articles by which the disadvantages of the prior art processes are reduced or overcome. In particular, the method of the invention substantially solves the problem of tack development since it prevents the development of tackiness even over the long term. In addition, the present method does not resort to the conventional method of chlorination to render the articles non-tacky. Thus, the present method does not include chlorination to render the articles non-tacky.

According to the present invention there is provided a method of making a non-tacky, powder-free neoprene article, preferably by dipping a former in a neoprene or neoprene copolymer latex, in which method one or more anionic anti-tack agents are used to reduce tack, the anti-tack agents being such as to prevent any significant development of tack for a period of up to at least seven days when the article is stored at 70° C. or at least 90 days when stored at 45° C.

By significant development of tack, we mean no more than an external surface tack rating (as herein defined) of about 2.0 when the storage period is 7 days at 70° C. (or 90 days at 45° C.), or no more than about 3.0 when the storage period is 14 days at 70° C. (or 180 days at 45° C.). Preferably, the tack rating will be below 2.0 after a period of 7 days at 70° C., or below 3.0 even after a period of 14 days at 70° C. or 180 days at 45° C.

In the case of a glove or other similar article, we prefer to coat the internal surface of the article with a layer of hydrogel to provide internal slip.

The invention thus includes a neoprene or neoprene copolymer glove or similar article which comprises internally, on the user-contacting surface, a layer of hydrogel, the glove or article also comprising one or more anti-tack agents.

The invention also encompasses the use of the anti-tack agents herein described to provide a long-term reduction in the development of tack in an article made from neoprene or neoprene copolymer latex.

We have found that whilst most known anti-tack (or anti-blocking) agents provide only an initial (and not long term) reduction in the development of tack, certain anti-tack agents are, unexpectedly, capable of providing a long-term reduction in the development of tack in neoprene articles. Such anti-tack agents include, but are not limited to, ammonium $C_{16}$–$C_{22}$ alkyl sulphates or phosphates, monovalent and divalent metal ion. $C_{16}$–$C_{22}$ fatty acid salts, (particularly stearates and their sodium, potassium, zinc, calcium and magnesium salts); ammonium $C_{16}$–$C_{22}$ fatty acid salts, and anionic wax emulsions. Particular examples include Rexanol (a commercial dispersion of potassium stearate) and Darvan L (an ammonium alkyl phosphate). It is to be understood that only certain anti-tack agents work effectively in the present process and that some anti-tack agents are clearly unsuitable. Anionic anti-tack agents are highly preferred and have been found to give excellent results. Non-anionic or cationic anti-tack agents do not give such good results.

The anti-tack agents used in accordance with the present invention provide not only an initial reduction in tackiness, but prevent any significant development of tack over the long term in articles made from neoprene or neoprene copolymer. By long term, we mean typically storage of the article for up to periods of three to five years at ambient temperature. This period may, however, include shorter periods when the articles are exposed to much higher temperatures, for example during shipping or other transport, when temperatures of up to 70° C. are not uncommon. Indeed, we have found with the present anti-tack agents that an acceptably low level of tackiness can be maintained even after storage of the article for up to one month at 70° C. (which treatment roughly equates to storage at ambient temperature for five years). It is desirable to have an external surface tack rating (as defined herein) of no more than about 3.0 even after three years' storage, and in many cases we have achieved results considerably better than this. Such an effect on the reduction of tackiness over the long term in neoprene articles is particularly surprising since certain of the present anti-tack agents (for example, Rexanol and Darvan L) do not prevent the development of tack over the long term when used with natural rubber latex.

A further advantage of the present anti-tack agents is that their ability to provide a long-term reduction in tackiness has been found to be unaffected by any other processing step including, in particular, irradiation of either the latex or the cured rubber. For example, in WO 99/43739 (see Examples 1 and 2) the use of gamma irradiation to sterilise the article leads to a sticky and discoloured glove and chlorination is unable to prevent this stickiness developing. ('Stickiness' is used in WO 99/43739 to cover both 'tackiness' and 'stickiness' as defined above.) By contrast, the present anti-tack agents are able to substantially prevent the development (both initially and in the long term) of any tackiness caused by irradiation. Thus, if desired, irradiation either to cure or sterilise the article or both can be used without adverse effect in the present method.

The present anti-tack agents also have the further advantage of providing a long term reduction in 'stickiness' (as well as tackiness) of neoprene articles, in that the articles do not stick to other material such as packaging.

We have also found that, unlike some other known anti-tack agents, the present anti-tack agents do not have any adverse effect on neoprene or upon the process of forming an article by dipping into a latex. Certain of the other known anti-tack agents interfere with the dipping process, and so cannot be used effectively in a dipping formulation, but this is not the case with the anti-tack agents presently described.

Heretofore, hydrogel coatings have typically been applied to the internal surface of articles such as gloves made from natural rubber latex, where they impart excellent dry- and damp-slip properties to facilitate donning (see, for example, EP-A-105613, EP-A-198514 and EP 199318). However, certain hydrogel materials do not coat very easily onto synthetic elastomeric materials such as nitrile or polyurethane rubbers. Rather surprisingly, however, we have now found that hydrogels suitable for slip coatings can be coated easily and conveniently onto coagulated neoprene and neoprene copolymer. A neoprene article with such a coating on the user-contacting surface is substantially free of internal tackiness and has excellent donning properties when in contact with either wet or dry skin.

Generally speaking, the articles (for example, gloves) are preferably made by initially dipping a suitably-shaped former into a solution of coagulant, followed by dipping into a formulation of compounded neoprene (or neoprene copolymer) latex in order to form a layer of coagulated latex on the former, and then leaching. Thereafter, however, instead of dipping into a powder followed by chlorination (as in WO 99/43739 for example), the coagulated latex on the former is preferably primed by dipping, for example, into dilute acid and, after rinsing and drying, is then preferably dipped, for example, into a solution of a hydrogel-forming polymer. Alternatively, a coagulant dip can be employed followed by dipping into a hydrogel latex. A series of dips into the hydrogel-forming polymer can be made if desired. The resulting hydrogel is heat dried so that the resulting hydrogel polymer is bonded to the rubber and so that the rubber is vulcanised and the polymer is simultaneously cured. After this step, the surface is then preferably treated with a physiologically acceptable surfactant, which can enhance the lubricity of the layer, particularly with respect to damp skin. Preferably, the glove is then washed in a solution of one or more anti-tack agents, although, alternatively, it is possible to include the anti-tack agents in the latex formulation if desired.

The articles of the invention are preferably made from a copolymer latex of 2-chloro-1,3-butadiene (chloroprene) and 2,3-dichloro-1,3-butadiene, although other suitable copolymers can be used if desired. Preferred copolymer latices are Neoprene 750 available commercially from Dupont, and polychloroprene Denka LV60N (Japan), the former being particularly preferred.

Typically, the latex solids are 40–47% (by weight of composition), with a preferred range of 45–46%.

In general, the compounded latex will comprise:

| Component | phr | Preferred |
|---|---|---|
| Neoprene or Neoprene Copolymer | 100 | 100 |
| Accelerators | 1.0–2.0 | 1.5 |
| Stabiliser | 0.6–1.2 | 0.9 |
| Vulcanising agent(s) | 4.0–18.0 | 12.0 |
| Pigment | 0.5–2.0 | 1.0 |
| Antioxidant | 1.0–3.0 | 1.0 |

We prefer to compound the latex in such a way as to give gloves of low modulus. Preferably, the gloves will have a M500 (modulus of elasticity at 500% elongation) not exceeding about 4 Mpa, more preferably not above 3 MPa. In addition, the latex will preferably be formulated so as to give a neoprene glove with an elongation at break (EB) of no lower than about 750%, with a preferred range of about 750–970%; and a tensile strength no lower than about 20 MPa, the preferred being about 20–30 MPa.

We have found that it is possible to use the presently disclosed anti-tack agents at various stages of the glove-making process. For example, if desired, one or more anti-tack agents may be compounded along with the neoprene or neoprene copolymer in the latex formulation. Alternatively, or in addition, the anti-tack agents may be used in a separate washing step, either before or after the glove is stripped from the former.

When used in the latex formulation itself, the anti-tack agents are preferably used at a concentration of between about 0.5–2.0 parts per hundred parts rubber (phr). Alternatively, when used in a separate washing step, the anti-tack agents are typically used at a concentration of between about 0.05 and about 0.20%, although lower or higher concentrations can be used if desired. We have found that our anti-tack agents are very effective at reducing the development of external surface tack during storage of both non-irradiated and irradiated gloves, the latter typically having higher initial values of surface tack.

We have also found that, in addition to the use of certain anti-tack agents, a reduction in surface tack can also be achieved by increasing the degree of cure of the glove. In a preferred aspect of the invention, both anti-tack agents and an increase in the degree of cure of the gloves are employed together to effect a reduction in the development of surface tack, although the anti-tack agents can be used alone if desired. The state of cure of the gloves can be increased, for example, by increasing the amount of sulphur employed in the compounded latex (for example, from 1 phr to 2 phr), or by an increase in the curing and/or drying temperatures used during processing of the gloves.

The hydrogel coating in the neoprene latex is preferably applied by dipping into a solution or dispersion of the hydrogel polymer.

Any suitable hydrogel polymer may be used in the present invention, although we prefer to use the hydrogel polymers which are copolymers of 2-hydroxyethyl methacrylate (HEMA) with methacrylic acid (MAA) and/or with 2-ethylhexyl acrylate (EHA) which are described in our European patent no. 105613. We prefer to use a copolymer comprising about 68 mol % HEMA, 14 mol % MAA, and 18 mol % EHA.

As noted above, once the hydrogel polymer layer has been applied to the rubber, bonded and cured, the process preferably includes the step of applying a solution of surfactant material to the glove, for example by tumbling in such a solution. Generally, the surfactant is applied after a washing step. The solution of surfactant material will preferably also comprise silicone which, in addition to the use of specific anti-tack agents can contribute to a reduction in the surface tack of the external surface of the glove (that is, the surface not coated with hydrogel). The specific anti-tack agents employed in the process of the invention can, if desired, be included in the surfactant solution along with any silicone (if present) or, alternatively, can be applied to the glove in a separate washing step either before or after treatment with the above surfactant. A separate washing step is preferred.

Preferred surfactants used to help provide lubricity to the glove, particularly with respect to damp skin, include N-cetylpyridinium chloride (CPC), sodium lauryl sulphate, N,N-dimethylhexadecylamine, ethylene oxide-polypropylene glycol condensates, distearyldimethylammonium chloride and hexadecyltrimethylammonium chloride. Others include those described in U.S. Pat. No. 3,813,695 (the "Podell patent"). Generally, the above compounds are used at a concentration of between 0.1% and 5%, the preferred range being 0.25–0.50%. Preferably the surfactant solution contains silicone (such as medical grade polydimethylsiloxane) at a concentration of at least 0.05% by weight of silicone (for example, 0.05 to 0.4% by weight).

After treatment of the glove with the surfactant solution and anti-tack agents (if not used earlier in the neoprene or neoprene copolymer latex), the glove is heated in order to fix the slip properties of the surfactant material coating. We have found that subsequent washing of the glove does not impair its damp- and dry-skin slip properties, neither does it lead to any significant increase in surface-tack.

The invention encompasses the production of any neoprene article, so long as it is made from a neoprene or neoprene copolymer latex. Preferably, the article is made by dipping a former into the rubber latex. The main articles we have in mind are gloves and condoms, particularly medical examination and surgeons gloves. Thicker, solvent-resistant gloves for industrial and drug-resistant applications are also envisaged. Typically, for a surgeons' glove the thickness of the synthetic elastomer layer will be about 0.12–0.30 mm, and the layer of hydrogel polymer will generally be 2–10 µm. For thicker, solvent-resistant gloves, the thickness of the synthetic elastomer layer will be about 0.25–0.75 mm and the hydrogel layer will be about 2–10 µm. An increase in the thickness of either the synthetic elastomer layer or the hydrogel polymer coating is preferably achieved by increasing the number of dips into the latex or polymer formulations respectively. Alternatively, the thickness of the synthetic elastomer layer can, for example, be increased by increasing the dwell time in the latex, the total solids content of the latex, or the concentration (specific gravity, SG) of the coagulate solution. The thickness of the hydrogel polymer layer could be increased by increasing the total solids content of the polymer solution.

In order that the present invention may be more fully understood, the following Examples are given by way of illustration only.

EXAMPLE 1

A thin walled surgeons' glove was made as follows. A glove shaped former was dipped into a solution of calcium nitrate (SG 1.10–1.20) and then dried at 90°–110° C. for 20–30 seconds. The former was then dipped into a compounded latex containing Neoprene 750 (total solids content (TSC)=40–46%). The latex contained Rhenocure, DPG and Zinc BuD as accelerators, sulphur and zinc oxide as vulcanising agents, Dehydol and Arylan as stabilisers, Wingstay L as antioxidant and Colanyl Blue A2R as pigment, according to the generalised formulation given above.

The coated former was dried at about 100° C. for about 1 minute, then beaded followed by leaching in water at 55°–60° C. for about 3 minutes, then dried in air for about 20 seconds. The surface of the latex on the former was then primed by dipping into a solution of 0.9–1.1% hydrochloric acid, rinsed in water, then dried in a stream of hot air. The coated former was then dipped into a solution of Hydrocote A (a terpolymer consisting substantially of 68 mole % HEMA, 14 mole % MAA, 18 mole % EHA) in industrial methylated spirits (IMS), beaded, and cured at 125°–145° C. for 25–30 minutes. The glove was then stripped from the former and washed in water, then washed in a solution containing 0.25% CPC, 0.075% silicone and 0.05% Darvan L (anti-tack agent) for 15–30 minutes. After washing in water, the glove was then dried at 90° C. for 120 minutes.

The total thickness (across one wall) of the above glove was 0.2 mm and it had the following physical properties:

M500=3.0 MPa

EB=930%

TS=26 MPa

The glove was substantially free of any surface tack with an external surface tack rating of 1.0. External surface tack was measured after storing the glove for one week at 70° C.

in this. Example and Examples 2–4. After storage, external surface tack was assigned as follows:

Assessment of Outer Surface Tack

1. Assign a tack rating by estimating the proportion of the glove cuff which is stuck to the rest of the glove after testing according to the following scoring system:

| Tack Rating | Description |
|---|---|
| 1.0 | Cuff is not stuck at all to the rest of the glove. |
| 1.5 | 25% or less of the cuff is stuck to the rest of the glove. |
| 2.0 | 25–50% of the cuff is stuck to the rest of the glove. |
| 2.5 | 50–80% of the cuff is stuck to the rest of the glove. |

2. If more than 80% of the cuff is still stuck to the rest of the glove after testing flick the glove twice and re-assess as described below:

| Tack Rating | Description |
|---|---|
| 3.0 | Cuff completely free of the rest of the glove. |
| 3.5 | Less than 20% of the cuff is stuck to the rest of the glove. |
| 4.0 | Approximately 50% of the cuff is stuck to the rest of the glove. |
| 4.5 | 50–80% of the cuff is stuck to the rest of the glove. |
| 5.0 | 80–100% of the cuff is stuck to the rest of the glove. |

3. Record the tack rating.
4. Repeat the test for a further 3 gloves per batch per ageing condition.
5. Calculate the average surface tack for the batch for each ageing condition.

The above procedure was repeated using different anti-tack agents. The results are tabulated below.

TABLE 1

| Anti-tack agent | Level used | External surface tack rating |
|---|---|---|
| None | 0% | 2.8–3.0 |
| Darvan L | 0.05% | 1.0 |
| Rexanol | 0.2% | 1.0 |
| Silicone | 0.02%, 0.10% and 0.20% | 1.3 |

EXAMPLE 2

Gloves were made as described in Example 1, but with the further addition of anti-tack agent to the latex formulation. After stripping from the former, the glove was processed as described in Example 1 but omitting the use of anti-tack agent in the washing solution. The glove was substantially free of any external surface tack with an external surface tack rating of 1.0 for each anti-tack agent employed, except for sodium stearate which gave 1.1. Results for different anti-tack agents are tabulated below.

TABLE 2

Examples of anti-tack agents that lead to gloves substantially free of any external surface tack.

| Anti-tack agent | Level used | External surface tack rating |
|---|---|---|
| None | 0 phr | 2.5–3.0 |
| Rexanol | 1.0 phr | 1.0 |
| Darvan L | 1.0 phr | 1.0 |
| Michem Lube 180 | 1.0 phr | 1.0 |
| Sodium stearate | 1.0 phr | 1.1 |
| Magnesium stearate | 1.0 phr | 1.0 |
| Calcium stearate | 1.0 phr | 1.0 |

EXAMPLE 3(a)

Example 1 (post-treatment with anti-tack agent) was repeated using further anti-tack agents. These were found to give much poorer results, as tabulated below.

TABLE 3

Examples of anti-tack agents that do not lead to a reduction in external surface tack.

| Anti-tack agent | Level used | External surface tack rating |
|---|---|---|
| None | 0% | 2.3 |
| Antilux | 0.05% and 0.10% | 2.6 |
| Michem Lube 180 | 0.05% and 0.10% | 2.5 |

EXAMPLE 3(b)

Example 2 was repeated using further anti-tack agents. These were found to give much poorer results, as tabulated below.

TABLE 4

Examples of anti-tack agents that do not lead to a reduction in external surface tack.

| | Anti-tack agent | Level used | External surface tack rating |
|---|---|---|---|
| | Coagulant WS | Destabilised latex | — |
| | None (control for 1 & 2 below) | 0 phr | 2.3 |
| 1 | Michem Lube 124 | 1.0 phr | 2.0 |
| 2 | Antilux | 1.0 phr | 2.1 |
| | None (control for 3 & 4 below) | 0 phr | 3.0 |
| 3 | PEG 1500 | 1.0 phr | 2.5 |
| 4 | PPG 425 | 1.0 phr | 2.8 |

EXAMPLE 4

Generally, external surface tack decreases with increasing glove thickness—that is, thinner gloves tend to have higher external surface tack than thicker gloves. A thinner glove with a single-wall thickness of 0.15 mm was made as described in Example 1 except that the TSC was reduced to 43% and coagulant solution SG was reduced to 1.16. The glove obtained was substantially free from external surface tack with an external surface tack rating of 1.0.

In the above Examples, all external surface tack ratings (including control values where no anti-tack agent has been used) were determined after ageing at 70° C. for 7 days.

| Definitions: | |
|---|---|
| Rexanol | Potassium stearate [C P Hall Company] |
| Darvan L | Ammonium alkyl phosphate [R T Vanderbilt Company, Inc.] |
| Michem Lube 180 | Anionic co-emulsion of carnauba and paraffin waxes [Michelman, Inc.] |
| Michem Lube 124 | Anionic microcrystalline wax emulsion [Michelman, Inc.] |
| Antilux | Paraffin wax [Bayer AG] |
| Coagulant WS | functional polyorganosiloxane [Bayer AG] |

The use of silicone as a post-treatment although it reduced external surface tack, led to a reduction in surface drag. That is, the gloves were increasingly slippy which is not a desired property.

Sodium, magnesium and calcium stearate gave reduced external surface tack, however, the additives reduced the initial and aged tensile strengths by 8–15%.

A number of conventional approaches to controlling external surface tack have been evaluated. These were all found to be less successful than the use of the anti-tack agents as described above. Comparative tests include:

EXAMPLE 5

Silicone

Silicone emulsion was sprayed onto the glove (as opposed to post-washing as in Example 1 above) in the tumble dryer just prior to drying them. This reduced external surface tack to some extent for gloves cured at low as well as high temperatures (see Table 5 below). High temperature curing leads to lower surface tack but does not overcome the tack problem.

TABLE 5

Effect of silicone on external surface tack

| | | Surface tack | | |
|---|---|---|---|---|
| Curing temp | Silicone spray | Initial | 1 day/70° C. | 7 days/70° C. |
| Low | No | 1.5 | 3.3 | 4.0 |
| | Yes | 1.0 | 1.5 | 3.3 |
| High | No | 1.0 | 2.5 | 3.5 |
| | yes | 1.0 | 1.0 | 2.3 |

Low temp curing = 100° C./14 min → 110° C./4 min → 120° C./4 min → 132° C./5 min
High temp curing = 125° C./8 min → 135° C./8 min → 145° C./9 min

EXAMPLE 6

Accelerator Level (ZBuD)

The level of accelerator used has no significant effect on the surface tack rating (see Table 6, below)

TABLE 6

Effect of accelerator level on external surface tack

| | | Surface tack | | |
|---|---|---|---|---|
| Curing temp | ZBuD (phr) | Initial | 1 day/70° C. | 7 days/70° C. |
| Low | 0.25 | 1.3 | 2.0 | 3.5 |
| | 0.50 | 1.3 | 2.5 | 4.0 |

TABLE 6-continued

Effect of accelerator level on external surface tack

| | | Surface tack | | |
|---|---|---|---|---|
| Curing temp | ZBuD (phr) | Initial | 1 day/70° C. | 7 days/70° C. |
| High | 0.25 | 1.0 | 2.0 | 2.8 |
| | 0.50 | 1.0 | 2.0 | 3.3 |

Low and high temp curing as in Table 5. Gloves not sprayed with silicone emulsion prior to drying.

EXAMPLE 7

Zinc Oxide Level

Increasing zinc oxide from 10 to 15 phr has no significant effect on the surface tack rating (see Table 7, below).

TABLE 7

Effect of zinc oxide level on external surface tack

| | | Surface tack | |
|---|---|---|---|
| Curing temp | ZnO (phr) | Initial | 7 days/70° C. |
| Low | 10 | 1.0 | 1.8 |
| | 15 | 1.0 | 1.8 |
| High | 10 | 1.0 | 1.8 |
| | 15 | 1.0 | 1.3 |

Low and high temp curing as in Table 5. Gloves not sprayed with silicone emulsion prior to drying.

EXAMPLE 8

Prevulcanisation

Prevulcanisation has been found to have no beneficial effect on surface tack (see Table 8, below). The latex was prevulcanised by heating at 50° C. for 24 hours, then cooled to ambient temperature (about 30° C.) and left to mature for 3 days. Latex matured for 4 days at ambient temperature was used as a control.

Gloves dipped from prevulcanised latex were found to stick to the formers more firmly when low temperature curing was used.

Extending the 50° C. heating by another 24 hours resulted in the latex being unusable, giving poor latex setting, uneven dipped films and split bead defects.

TABLE 8

Effect of prevulcanisation of latex on external surface tack

| | | Surface tack | | |
|---|---|---|---|---|
| Curing temp | Prevulcanisation | Initial | 1 day/70° C. | 7 days/70° C. |
| Low | No [control] | 1.3 | 1.8 | 1.5 |
| | Yes | 1.0 | 1.8 | 1.5 |
| High | No [control] | 1.0 | 1.8 | 1.8 |
| | yes | 1.0 | 1.5 | 1.5 |

Low and high temp curing as in Table 5. Gloves not sprayed with silicone emulsion prior to drying.

EXAMPLE 9

Chlorination

An evaluation of the effect of chlorination on the surface tack of the gloves was carried out using 4 levels of available chlorine—600, 900, 3000 and 4000 ppm and 150 mL chlorinating solution per glove. At available chlorine levels of 900 ppm and above, all gloves exhibited serious internal and external surface tack after drying. Qualitatively, the degree of tack increased with increasing chlorine strength. In fact, after chlorination even wet gloves were found to be stuck externally while awaiting drying. For gloves chlorinated at 600 ppm, 70% of the gloves stuck internally. The gloves were sprayed with silicone emulsion before drying and even with this treatment, the gloves exhibited high external surface tack (see Table 9, below).

TABLE 9

Effect of chlorination on external surface tack.

| External surface tack | | |
|---|---|---|
| Initial | 4 hours/70° C. | 1 day/70° C. |
| 1.0 | 2.0 | 3.0 |

Gloves sprayed with silicone emulsion prior to drying.

In contrast to the above results, the external surface tack value of gloves treated with an anti-tack agent (either in the latex formulation or in a separate washing step) was found not to increase above 1.0, even despite storage at 70° C. for up to 7 days.

The invention claimed is:

1. A method of making a non-tacky, powder-free neoprene article, said method comprising dipping a former in a neoprene or neoprene copolymer latex, in which method one or more anionic anti-tack agents are used to reduce tack, wherein the or each anti-tack agent is an ammonium $C_{16}$–$C_{22}$ alkyl sulphate or phosphate, a monovalent or divalent metal ion $C_{16}$–$C_{22}$ fatty acid salt, or an ammonium $C_{16}$–$C_{22}$ fatty acid salt, the anti-tack agents being such as to prevent any significant development of tack for a period of up to at least seven days when the article is stored at 70° C. or at least 90 days when stored at 45° C., which method does not include chlorination.

2. A method according to claim 1 wherein the external surface tack rating developed is below 2.0 after seven days at 70° C.

3. A method according to claim 1 wherein the said tack rating is below 3.0, after a period of 14 days at 70° C.

4. A method according to claim 1 wherein the anti-tack agent is selected from the group consisting of potassium stearate, a sodium, zinc, calcium or magnesium $C_{16}$–$C_{22}$ fatty acid salt, and an ammonium $C_{16}$–$C_{22}$ alkyl phosphate.

5. A method according to claim 1 wherein the said anti-tack agent is included in a latex formulation prior to formation of said article or, alternatively, or in addition, the anti-tack agent is used in a washing step after said article has been formed.

6. A method according to claim 5 wherein said article is washed in a solution of said anti-tack agent.

7. A method according to claim 5 wherein, when said anti-tack agent is included in a latex formulation, and is present at a concentration of between 0.5–2.0 parts per hundred parts rubber (phr), or when used in a washing step after said article has been formed, it is present at a concentration of from 0.05 to 0.2% by weight of the washing formulation.

8. A method according to claim 1 wherein said method further includes the step of subjecting the said article to an irradiation step.

9. A method according to claim 1, wherein said method further includes the step of increasing the state of cure of the article, preferably by employing 2 phr or more of sulphur in a neoprene or neoprene copolymer latex.

10. A method according to claim 1, wherein said method further includes the step of providing said article with a layer of hydrogel to provide slip.

11. A method according to claim 1, wherein the said article is a glove or a condom.

12. A powder-free neoprene or neoprene copolymer glove or condom which is chlorine free, comprising one or more anti-tack agents wherein the or each anti-tack agent is an ammonium $C_{16}$–$C_{22}$ alkyl sulphate or phosphate, a monovalent or divalent metal ion $C_{16}$–$C_{22}$ fatty acid salt, an ammonium $C_{16}$–$C_{22}$ fatty acid salt or an anionic wax emulsion and a layer of hydrogel on an internal, user-contacting surface, and wherein the glove or condom does not develop any significant tack for a period of up to at least seven days when stored at 70° C. or at least 90 days when stored at 45° C.

13. A method according to claim 1 wherein the external surface tack rating developed is below 1.5 after seven days at 70° C.

14. A method according to claim 1 wherein the said tack rating is below 2.0 after a period of 14 days at 70° C.

15. A method according to claim 1 wherein the said tack rating is below 3.0 after a period of 180 days at 45° C.

16. A method according to claim 1 wherein the said tack rating is below 2.0 after a period of 180 days at 45° C.

17. A method according to claim 4 wherein the monovalent or divalent metal ion $C_{16}$–$C_{22}$ fatty acid salt, is a stearate and their sodium, potassium, zinc, calcium and magnesium salts.

18. A method according to claim 1, wherein the said glove is a medical examination or surgeons glove.

19. The method according to claim 1, wherein the monovalent or divalent metal ion $C_{16}$–$C_{22}$ fatty acid salt is one selected from stearates and their sodium, potassium, zinc, calcium and magnesium salts.

* * * * *